United States Patent
Weiner

[19]

[11] Patent Number: 6,165,151

[45] Date of Patent: *Dec. 26, 2000

[54] APPARATUS AND METHODS FOR CONTROL OF INTRAVENOUS SEDATION

[76] Inventor: Daniel L. Weiner, 1755 York Ave., New York, N.Y. 10128

[ * ] Notice: This patent issued on a continued prosecution application filed under 37 CFR 1.53(d), and is subject to the twenty year patent term provisions of 35 U.S.C. 154(a)(2).

[21] Appl. No.: 08/922,887

[22] Filed: Sep. 3, 1997

Related U.S. Application Data

[60] Provisional application No. 60/025,054, Sep. 3, 1996.

[51] Int. Cl.$^7$ .................................................... A61M 31/00

[52] U.S. Cl. .............................................. 604/66; 604/250

[58] Field of Search .................................. 604/65–67, 27, 604/30, 31, 34, 246, 250

[56] References Cited

U.S. PATENT DOCUMENTS 5,298,021  3/1994  Sherer ........................................ 604/66
5,674,190  10/1997  Kelly .......................................... 604/4

*Primary Examiner*—Corrine McDermott
*Attorney, Agent, or Firm*—Levisohn, Lerner, Berger & Langsam

[57] ABSTRACT

Apparatus and methods for controlling the administration of intravenous drugs for sedation of a patient. Safe and controlled levels of sedation are provided by the use of a system for continous monitoring of patient pulse oximetry levels during the sedative's adminstration. Adequate levels of sedation that are clinically desirable are accomplished by the device, safely and smoothly, without the risk of respiratory depression. Preestablished oximetry ranges are provided before and/or during administration of the analgesic as the maximum and minimum acceptable saturation levels. Levels of sedation are continuously adjusted in response to increases or drops in oxygen saturation to smoothly maintain the saturation levels within the preestablished parameters.

14 Claims, 2 Drawing Sheets

APPARATUS AND METHODS FOR CONTROL OF INTRAVENOUS SEDATION

RELATED APPLICATIONS

The present application claims the priority of U.S. Provisional Application Ser. No. 60/025,054, filed Sep. 3, 1996, whose contents are fully incorporated herein by reference.

FIELD OF THE INVENTION

The present invention relates to apparatus and methods for controlling the administration of intravenous sedation to a patient.

BACKGROUND OF THE INVENTION

Currently, clinically sedation is delivered by multiple single bolus injections into an intravenous line for administration to a patient. Following delivery of the sedation, the patient's clinical signs and pulse oximeter readings are monitored by the anaesthesiologist, to avoid overmedication of the patient. As a general rule, increased levels of drug induced sedation and analgesia are directly associated with a parallel and progressive increase in respiratory depression. Thus, monitoring the patient's clinical signs and pulse oximeter readings is of significant importance to prevent sedation-related respiratory depression or respiratory arrest.

SUMMARY OF THE INVENTION

It is an object of the present invention to provide apparatus and methods for providing adequate and consistent levels of sedation.

It is a further object of the present invention to provide apparatus and methods for continuously controlled monitoring and administration of a medication or analgesic to a patient where respiratory depression is a risk.

It is a further object of the present invention to eliminate the potential problems of patient overdose, respiratory depression or respiratory arrest.

Further objects of the invention will become apparent in conjunction with the disclosure herein.

In accordance with the present invention, apparatus and methods are provided for improved delivery of sedation, analgesic, or anesthetic to a patient. Safe and controlled levels of sedation are provided by the use of a system that continuously monitors patient pulse oximetry levels and adjusts the rate of delivery of the drug within the preselected safe parameters for that particular patient. Preestablished oximetry ranges are provided before and/or during administration of the drug as the maximum and minimum acceptable saturation levels. Levels of sedation are continuously adjusted in response to increases or drops in saturation to maintain the patient's oxygen saturation levels within the preestablished parameters.

DETAILED DESCRIPTION OF THE INVENTION AND THE PREFERRED EMBODIMENTS

As is well known in the art, the administration of sedative, analgesia or anesthetic to a patient during a medical procedure, such as surgery, is itself associated with a concurrent effect on patient respiration. In general, increased levels of drug induced sedation and analgesia are directly associated with a parallel and progressive increase in respiratory depression. For clarity, we use the terms sedative or sedation to collectively refer to any chemical agent which is administered and controlled to a patient during a medical procedure and which can have a depressive effect on patient respiration. Thus, the term is collectively used herein to refer to sedatives, analgesics, anaesthetics, or the like.

Currently, it is the constant task of the anesthesiologist during a medical procedure to continually observe the vital signs of the patient to monitor the sedation's effect. According to this practice of the art, monitoring of vital signs is a continuous process which is accomplished, inter alia, by supervision of pulse oximetry readings to determine ongoing levels of oxygen saturation. This process of monitoring saturation levels without interruption can be difficult, however, over extended periods. In addition to the problems associated with fatigue, the procedures and events occurring in the operating room can give rise to distractions or other interruptions of the anaesthesiologist's attention.

In general, acceptable levels of oxygenation in a patient are predetermined by the anaesthesiologist prior to the procedure based on such factors as the patient's age and medical history. Upon establishment of a desired range of saturation levels, it is the task of the anaesthesiologist to continually supervise the patient to ensure that oxygen saturation remains within the acceptable the range, and does not exceed the maximum or minimum limits. Upon observing that saturation levels have exceeded acceptable limits, appropriate steps are taken to quickly reduce or increase oxygen saturation, as necessary. This reactive approach, and the quick steps effected to bring saturation within acceptable levels can result in an uneven course of sedative administration and treatment, with erratic and unpredicable changes in oxygen saturation and the vital signs of the patient. Accordingly, in accordance with the present invention, a method and apparatus is provided for maintaining a uniform, continually regulated flow of sedative to a patient which is adjusted based upon oxygen saturation as measured by pulse oximetry levels.

Figure 1:
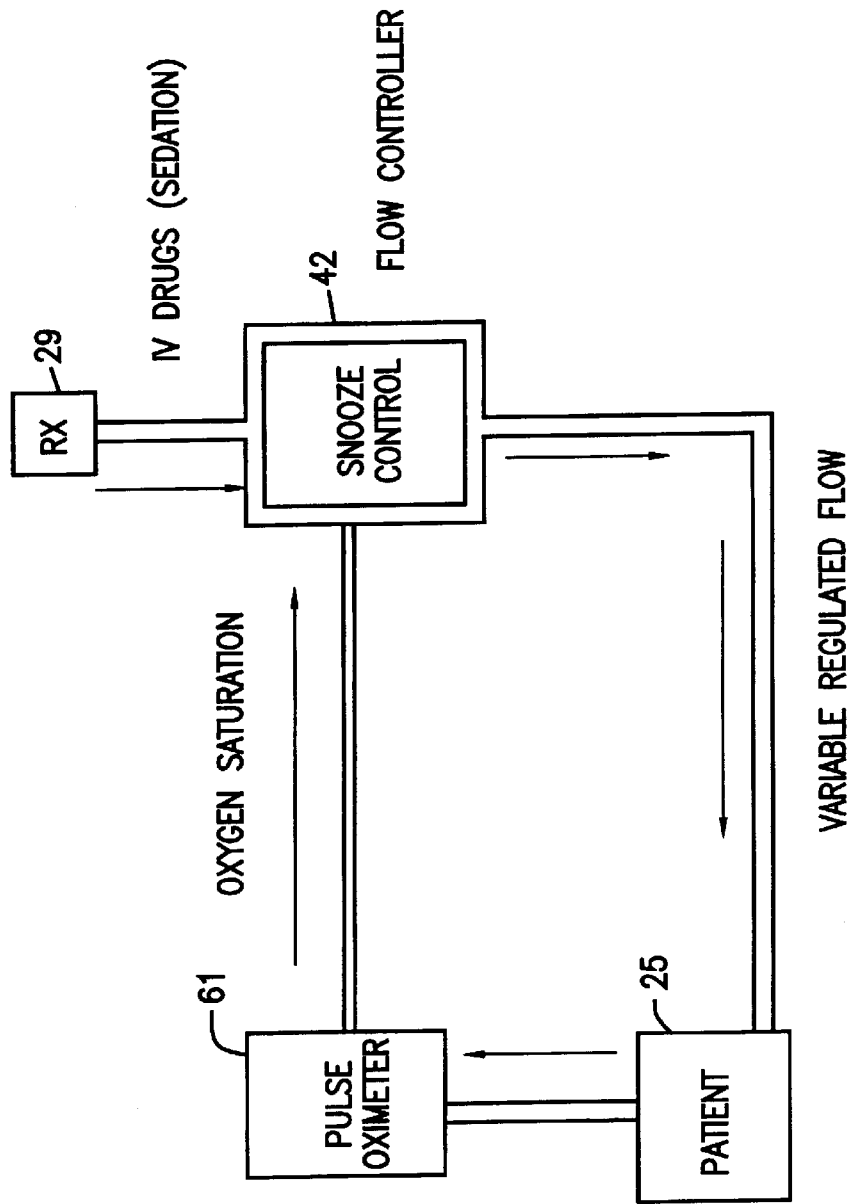
FIG. 1 is a flowchart illustrating the method in accordance with the present invention.
Figure 2:
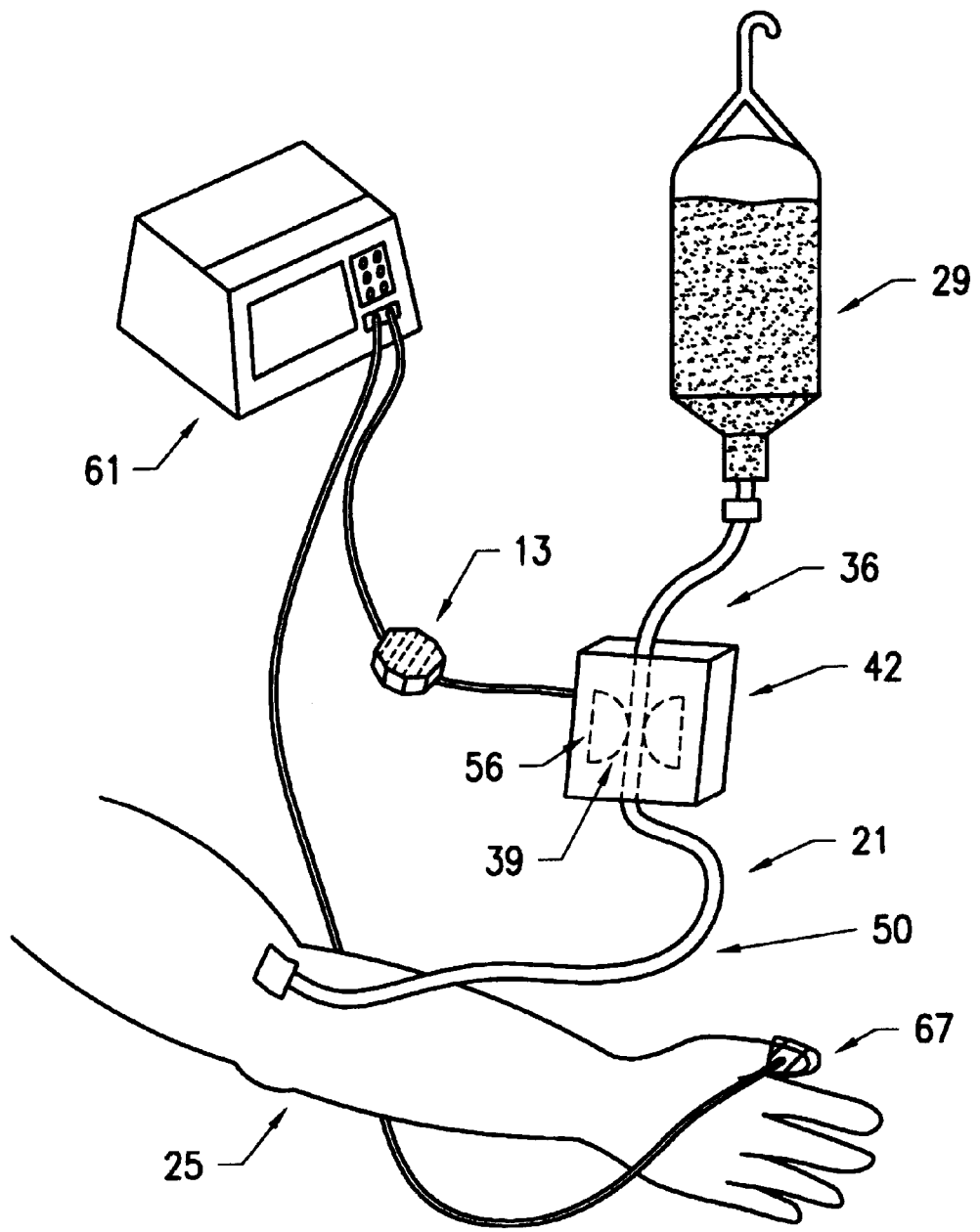
FIG. 2 is a schematic illustration of the apparatus of the present invention, including the controller and the variable pressure clamp. The controller of the invention is attached both to a pulse oximeter and to a flow regulator, with the flow regulator in turn being connected to an intravenous line which delivers the drug to the patient.

As shown in FIGS. 1 and 2, in accordance with the present invention, a direct interrelationship is established between the flow of intravenous drugs and the pulse oximetry readings of a patient. As shown in FIG. 2, an intravenous line (IV) 21 extends from intravenous bag 29 for administration of sedative from intravenous bag 29 into a patient 25. Intravenous line 21 and IV bag 29 are standard IV lines and bags such as are common and known in the art. Intravenous line 21 is a continous segment extending from the intravenous bag 29 to the patient.

While receiving the infusion of sedative through the IV, patient 25 is provided with a pulse oximetry sensor 67 connected to pulse oximeter 61. Pulse oximetry sensor 61 is a sensor for transillumination of a blood perfused portion of the body to measure light extinction during transillumination, as is known in the art. The sensor is usually mounted on a digit, such as a fingertip (as shown in the figure), although any blood perfused tissue is acceptable. The sensor conforms to and with the cutaneous layer of the blood perfused portion of flesh upon which the sensor is placed. A light source is mounted to a first end portion of the sensor, and a photosensor is mounted to the second end portion of the sensor. The sensor is suitably windowed so that light is allowed to take an optical path through the finger. Light passes from the light source mounted to the first end portion, through the finger, to the photosensor mounted on the second end portion. By measuring received light, the photosensor allows continuous monitoring of the vital signs of a patient during a medical procedure.

Transillumination of the blood perfused portion of the body yields information that includes, for example, oxygen saturation of the hemoglobin in the blood flow, the volume of individual blood pulsations supplied, and the rate and rhythm of blood pulsations. Specifically, for oxygen saturation of the hemoglobin, for a given wavelength of light transmitted through the patient's digit, there is a known extinction coefficient B. Given B, by measuring the intensity of diffused light received by the sensor 67, the oxygen saturation of the patient's blood can be computed and displayed.

During a surgical procedure, the oxygen saturation of the patient is monitored and displayed by pulse oximeter 61. Pulse oximeter 61 provides a continuous realtime display of saturation levels, based on the readings from sensor 67.

In accordance with the invention, pulse oximeter 61 is connected to controller 13. Controller 13 is thereby provided with instant information regarding the patient's saturation levels which are being monitored by pulse oximeter 61. The controller 13 is further connected to a flow control regulator 42 such as a variable pressure clamp. Flow regulator or variable pressure clamp 42 is attached to intravenous line 21. As noted previously, intravenous line 21 is a continuous line extending from intravenous bag 29 to the patient 25. For reference purposes, the portion of the intravenous line 21 above and prior to variable pressure clamp 42 is referred to herein as preregulated segment 36, while the portion of the intravenous line 21 below and after variable pressure clamp 42 is referred to as postregulated segment 50. The portion of the intraveneous line where pressure is exerted, within the variable pressure device 42, is referred to as compression segment 39.

The flow control regulator is a regulating device for controlling the flow of sedative or intravenous solution from the IV bag to the patient. Many such devices are known in the art. In the preferred embodiment, a mechanical device will exert variable pressure.

As shown in FIG. 2, variable pressure device or clamp 42 is a device capable of providing variable pressure on the intravenous line 21, in response to a signal from controller 13. Variable pressure device 42 includes means for receiving a signal from controller 13 and means for changing the diameter of the lumen of the IV line by compressing the IV line to immediately increase or decrease flow as needed. For example, as shown in the figure, in response to a signal from controller 13, pressure blocks 56 can move together to exert pressure on compression segment 39 of IV line 21, or apart to reduce the pressure thereon. When the two pressure blocks 56 move inward, they serve to compress IV line 21 at compression segment 39, reducing flow therethrough. Upon receipt of an appropriate signal from the controller, pressure blocks 56 can move outward in the opposite direction to reverse the effect, to the extent desired, until IV line 21 is restored to its original diameter at compression segment 39.

Variable pressure device 42 can be set to have as many compression positions as possible, each of which is associated with a different IV line diameter. For example, in one embodiment, clamp 42 has four separate positions which can be controlled by controller 13. In position one, clamp 42 is in its widest diameter state such that no pressure is exerted on intravenous line 21, and sedative flows unimpeded into patient 25. In position two, the portion of clamp 42 in contact with the IV line 21 decreases in diameter to provide a moderate degree of pressure on IV line 21. This pressure slightly reduces the diameter of the IV line, reducing intravenous and sedative flow into the patient. In other words, flow from preregulated segment 36 of IV line 21 is partially blocked, by the narrowing of the diameter of IV line 21 at clamp 42, reducing flow to postregulated segment 50 and thus to patient 25. In position three, clamp 42 is even more reduced in diameter to provide increased pressure on the IV line, reducing intravenous and sedative flow yet further. In position four, clamp 42 is closed to its smallest diameter state, exerting pressure which completely closes IV line 21 preventing any intravenous or sedative flow into postregulated segment 50 or patient 25. Although four positions are provided herein for illustration, more or less can, of course, be provided as desired.

Prior to the procedure, the medical practitioner programs controller 13 with the acceptable preestablished range of oxygen saturation levels which are considered acceptable for the patient during the procedure. The acceptable saturation levels generally varies with the particular patient, and will be set based on the practitioner's experience, judgment, and assessment of the patient's age, health, medical history and so forth. In a young healthy adult, for example, acceptable oxygen saturation may be preestablished at 80–85%. Preestablished saturation levels may be set before the procedure at any combination of minimim and maximum saturation levels which the anaesthesiologist considers acceptable. Acceptable levels are programmed into the controller by inputting the acceptable ranges into the controller 13 through the input keys located on its surface. The preestablished range can be modified during the course of the procedure if desired or necessary.

As shown in FIG. 1, as sedative is administered to the patient during the procedure, a continuous flow of pulse oximetry readings will be provided to the pulse oximeter 61 based on the input from sensor 67. Pulse oximeter 61 is a pulse oximeter having means for providing an pulse oximetry signal based on the oxygen saturation levels of the patient which have just been calculated by the pulse oximeter. Following calculation, pulse oximeter 61 feeds a continuous signal to controller 13 to inform the controller 13 of current patient oxygen saturation levels. Controller 13 includes means for receiving the signal from the pulse oximeter 61, and means for determining the patient's ongoing oxygen saturation levels based on the received signal. The construction of controller 13 and pulse oximeter 61 are a matter of ordinary skill, as would be apparent to one of ordinary skill in the art.

Upon determining the patient's oxygen saturation based on the signal from pulse oximeter 61, controller 13 compares the oxygen saturation levels calculated by pulse oximeter 61 with the acceptable levels previously input into the controller. Controller 13 includes means for providing a control signal to flow regulator or variable pressure clamp 42, with the flow regulator in turn including means for receiving that control signal and responding thereto by varying the flow of intravenous solution through the IV line (e.g., by varying the pressure exerted on the IV line 21, as discussed above).

If the saturation levels are below the minimum level set in the preestablished range, the controller 13 sends a signal to variable pressure device 42 to decrease the diameter of IV line 21, which decreases the level of sedative being administered to patient 25, reduces respiratory depression, and increases oxygen saturation levels. Conversely, if the saturation levels are above the maximum level set in the range, the controller 13 sends a signal to variable pressure clamp 42 to open up the diameter of the IV line, which increases sedative flow and respiratory depression, and decreases oxygen saturation. It is preferred that the regulation of flow be accomplished by the compression of the IV line, however, it is understood that other methods for regulating the flow of sedative by a controller may be accomplished. Such are considered to be within the scope of the invention when sedation flow regulation is provided based upon feedback from a pulse oximeter.

In the present invention, the regulation of sedative flow by controller 13 is a continuous process, in which the controller continually monitors and adjusts flow in response to the input from the signal from the pulse oximeter 61. In this way, a continual, smoothly adjusted and finely regulated level of sedative is administered to the patient, based on the feedback from the pulse oximeter. Accordingly, the anaesthesiologist can continue to monitor the vital signs of the patient, however, the monitoring process is done with a continual backup, which is designed to ensure that oxygen saturation levels are guarded from exceeding preestablished limits.

This maintenance of a controlled and reduced O2 saturation within a predetermined range is clinically desirable and will insure adequate and consistent levels of sedation that is continuous, uniform and predictable. It can eliminate potential problems of patient overdose, respiratory depression or respiratory arrest, due to sedation dosages during a medical procedure. In addition, it can enable the operative team to focus its attention and efforts on the surgery in a stable environment without distractions relating to the patient's ongoing sedation levels.

Having described this invention with regard to specific embodiments, it is to be understood that the description is not meant as a limitation since further modifications or variations may suggest themselves to those skilled in the art. It is intended that the present application cover such modifications, variations and embodiments as fall within the scope of the appended claims.

I claim:

1. In combination, an apparatus for regulating the flow of sedative supplied from a supply source through an intravenous line to a patient comprising:

a supply source for supplying sedative, an intravenous line connected thereto a controller unit, said controller unit receiving a pulse oximetry signal from a pulse oximeter, said controller unit generating a control signal based on said pulse oximetry signal; and, a flow control regulator, said flow control regulator receiving said control signal, said flow control regulator physically constricting said intravenous line and regulating the flow of sedation to a patient responsive to said control signal from said controller, said flow control regulator being located between the supply source and the patient to control the flow of sedation.

2. An apparatus as claimed in claim 1, wherein said controller unit further comprises means for inputting a range of acceptable oxygen saturation levels into said controller unit.

3. An apparatus as claimed in claim 4, wherein said controller unit provides said control signal to said flow regulator based upon said range of acceptable oxygen saturation levels and based upon said pulse oximetry signal.

4. An apparatus as claimed in claim 1 wherein said intravenous line has a cross-sectional area that is controlled by said flow control regulator.

5. An apparatus as claimed in claim 4, wherein said control regulator control is a variable pressure device for regulating the diameter of said intravenous line.

6. An apparatus as claimed in claim 5, wherein said flow control regulator reduces the diameter of said intravenous line in response to a drop in oxygen saturation levels as measured by the pulse oximeter.

7. An apparatus as claimed in claim 1 further comprising a gravity control system for supplying sedative to a patient from said supply source through said intravenous line with gravity causing the sedative to flow through said intravenous line.

8. An apparatus for regulating the flow of sedative supplied from a supply source through an intravenous line to a patient comprising:

a controller unit, said controller unit setting a predetermined range of acceptable oxygen saturation levels, said predetermined range of acceptable oxygen saturation levels including a minimum acceptable oxygen saturation level, said controller unit receiving a pulse oximetry signal from a pulse oximeter, said controller unit generating a control signal based on said pulse oximetry signal and said predetermined range of acceptable oxygen saturation levels; and, a flow control for regulator, said flow control regulator receiving said control signal, said flow control regulator regulating the flow of sedation to a patient through said intravenous line responsive to said control signal from said controller, said flow control regulator being physically capable of constricting the flow of sedation through said intravenous line.

9. An apparatus as claimed in claim 8, wherein said flow control regulator is a variable pressure device for compressing the diameter of the intravenous line.

10. An apparatus as claimed in claim 9, wherein the intravenous line has a normal, non-compressed diameter, and wherein said variable pressure device can compress said intravenous line into at least one diameter smaller than said normal, non-compressed diameter.

11. An apparatus as claimed in claim 9, wherein the intravenous line has a normal, non-compressed diameter, and wherein said variable pressure device can compress said intravenous line into a plurality of diameters smaller than said normal, non-compressed diameter.

12. An apparatus as claimed in claim 9, wherein said controller sends said control signal to said flow control regulator to decrease the diameter of the intravenous line in response to a drop in the patient's oxygen saturation level.

13. An apparatus as claimed in claim 12, wherein said control signal is sent in response to a drop in the patient's oxygen saturation level below said minimum acceptable oxygen saturation level.

14. An apparatus as claimed in claim 8 further comprising a gravity control system for supplying sedative to a patient through said intravenous line with gravity causing the sedative to flow through said intravenous line.

* * * * *